United States Patent [19]

Struble

[11] Patent Number: 4,477,008
[45] Date of Patent: Oct. 16, 1984

[54] STAPLER
[75] Inventor: Kent R. Struble, Woodbury, Minn.
[73] Assignee: Minnesota Mining and Manufacturing Company, Saint Paul, Minn.
[21] Appl. No.: 552,025
[22] Filed: Nov. 18, 1983

Related U.S. Application Data

[63] Continuation of Ser. No. 299,068, Sep. 3, 1981, abandoned.

[51] Int. Cl.³ ............................................. A61B 17/04
[52] U.S. Cl. ................................. 227/19; 128/334 R; 227/120; 227/129; 227/DIG. 1
[58] Field of Search ............... 128/334 R; 227/19, 83, 227/120, 129, 156, DIG. 1

[56] References Cited

U.S. PATENT DOCUMENTS

| | | | |
|---|---|---|---|
| 3,225,996 | 12/1965 | Mallina | 227/DIG. 1 |
| 3,244,342 | 4/1966 | Boorlakov et al. | 227/DIG. 1 |
| 3,613,683 | 10/1971 | Kees et al. | 128/325 |
| 3,827,277 | 8/1974 | Weston | 227/DIG. 1 |
| 3,906,957 | 9/1975 | Weston | 227/DIG. 1 |
| 4,166,466 | 9/1979 | Jarvik | 227/DIG. 1 |
| 4,185,762 | 1/1980 | Froehlich | 227/DIG. 1 |
| 4,202,480 | 5/1980 | Annett | 227/DIG. 1 |
| 4,256,251 | 3/1981 | Moshofsky | 227/19 X |

FOREIGN PATENT DOCUMENTS

| | | |
|---|---|---|
| 2037710 | 2/1971 | Fed. Rep. of Germany . |
| 2154047 | 5/1973 | France . |

Primary Examiner—Paul A. Bell
Attorney, Agent, or Firm—Donald M. Sell; James A. Smith; William L. Huebsch

[57] ABSTRACT

A stapler for applying a staple to join living tissue, a major portion or all of which stapler can be made as a unitary molding. The stapler comprises a body adapted to support the staple adjacent an anvil, and a ram adapted to close the staple around the anvil slidably mounted on the body. A single toggle joint linkage between the body and ram can be squeezed toward the body to bend the toggle joint linkage about axes parallel to the side surface of the staple and move the ram so that the staple is closed.

12 Claims, 12 Drawing Figures

STAPLER

This is a continuation of application Ser. No. 299,068 filed Sept. 3, 1981 now abandoned.

TECHNICAL FIELD

This invention relates to staplers of the type adapted to join living tissue.

BACKGROUND ART

Staplers adapted to join living tissue are well known. The earliest known type of staplers for such use were designed to be reusable and included high quality castings and machined parts of easily cleanable and sterilizable materials such as stainless steel (see, for example, the staplers described in U.S. Pat. Nos. 3,643,851, 3,819,100 and 3,873,016). Such staplers typically are sterilized before each use in sterilizing equipment located at the facility (e.g., a hospital) in which they are used. The high cost of disassembling, cleaning and sterilizing such staplers before each use makes their use uneconomical where only a few staples are to be applied to a patient. Also the time needed for the sterilization procedure between successive uses of such staplers further restricts their use where a series of patients may each need the application of only a few staples, such as may occur in a hospital emergency room.

More recently introduced types of staplers for joining living tissue are designed to be disposable (see for example the staplers described in U.S. Pat. Nos. 4,109,844, 4,202,480 and 4,256,251). Such disposable staplers are made of relatively inexpensive parts such as plastic moldings and metal stampings that are sterilized during manufacturing and are packaged so that they remain sterilized until they are used. Such staplers are intended for use on only one patient, however. Thus, while due to the savings in cleaning and sterilization costs their use may be less expensive than that of reusable staplers where approximately the quantity of staples packaged in the stapler is to be used (e.g., 15 to 30 staples), and the use of different sterilized staplers precludes problems of waiting for a single stapler to be resterilized between usages; the use of such disposable staplers is still uneconomical where only a few staples (e.g., less than 10) are to be used in a patient.

Of the known prior art staplers of the above types, the one having a structure closest to the present invention appears to be the disposable type stapler described in U.S. Pat. No. 4,202,480. That stapler comprises an elongate body having a guide surface adjacent a front end of the body, and an anvil transversely centered at the front end projecting at a right angle to the guide surface. Means are provided for feeding staples onto the guide surface with points of the staples adjacent the front end of the body, and a ram is mounted on the body for movement from an open position to a closed position to cause the ram to bend a staple on the guide surface closed around the anvil. The ram can be manually moved by a pair of toggle joint linkages attached between a rear end of the body and the ram. The toggle joint linkages are opposed and project away from opposite sides of the body when the ram is in its retracted position so that pressing the toggle joint linkages toward each other in a direction transverse to the guideway will move the ram from its open to its closed position. An improved version of that stapler has been sold for over 12 months under the trademark "Precise" by Minnesota Mining and Manufacturing Company of St. Paul, Minn., and has been found to be an effective mechanism for applying staples. Like the other disposable staplers on the market, however, its mechanism is too complex to make the stapler economical to apply only a few staples.

DISCLOSURE OF THE INVENTION

The present invention provides an effective, inexpensive, disposable-type stapler that is economical to use when only a small number of staples (e.g., 1 to 10) are to be applied to a patient.

According to the present invention there is provided a stapler which, like the stapler described in U.S. Pat. No. 4,202,480, comprises an elongate body, a guide surface adjacent a front end of the stapler, and an anvil transversely centered at its front end projecting at a right angle to the guide surface. Means are provided for positioning a staple on the body adjacent the anvil with a side surface of the staple along the guide surface and the points of the staple adjacent the front end of the body. A ram having an end surface adapted to engage the edge surface of the staple opposite its points is mounted on the body for movement from an open position with the end surface of the ram spaced from the anvil to afford space for the open staple therebetween, to a closed position to cause the end surface of the ram to engage and bend the staple closed around the anvil. Also a toggle joint linkage is attached between the rear end of the body and the ram so that the toggle joint linkage projects from the body in the open position of the ram and is manually movable toward the body to move the ram to its closed position.

Unlike the stapler described in U.S. Pat. No. 4,202,480, however, the stapler according to the present invention has a novel greatly simplified design that includes only a single toggle joint linkage in which pivotal movement of the toggle joint linkage occurs around axes parallel to the guide surface; which toggle joint linkage is activated to form the staple by pressing it toward the body of the stapler.

Preferably the stapler according to the present invention is adapted to use with a generally W-shaped staple of the type described in U.S. Pat. No. 4,185,762 which requires a less complex and rugged ram to form the staple than does the generally U-shaped staple described in U.S. Pat. No. 4,202,480.

In a preferred, very inexpensive embodiment, the body, the ram, and first and second drive members which provide the toggle joint linkage of the stapler are formed in their entirety as a unitary polymeric molding and are joined by thin, flexible, transverse sections of the molding. The molding is elongate with the body at one end and the ram at the other. A single staple can be releasably loaded on the means for positioning a staple (which is provided by grooves that receive the staple with its center portion against the anvil), and the stapler can be packaged and sterilized. Before use, the thin transverse sections of the molding are bent and the ram is engaged with means mounting the ram on the body for movement between its open and closed position (which can be done by the manufacturer prior to packaging or by the user subsequent to opening the packaging), whereupon the toggle joint linkage projects from one side of the body and can be squeezed toward the body to close the staple and engage it to close the disunited tissue or skin of a patient. The ram may then be retracted, a second sterilized staple loaded into the means for positioning a staple, and the second staple applied to a patient; or more conveniently, the used stapler may be discarded and a second stapler used to apply a second staple. In either event the stapler provides a quick, convenient, inexpensive device for applying a few staples that is wholly suitable for use where a series of applications of a few staples each are desired such as in an emergency room of a hospital.

Also preferably, the stapler includes means for biasing the ram to its open position that facilitates withdrawing the anvil from within the closed staple, and that can also facilitate reloading the stapler described should that be desired. Preferably the means for biasing comprises means for mounting the body to the first drive portion so that the first drive portion must be resiliently bent to move the ram to its closed position and will recover to return the ram to adjacent its open position upon the release of force applied to the toggle joint linkage; however more conventional springs can also be used.

BRIEF DESCRIPTION OF DRAWING

The present invention will be more thoroughly described with reference to the accompanying drawing wherein like numbers refer to like parts in the several views, and wherein.

DESCRIPTION OF THE PREFERRED EMBODIMENTS

Figure 1:
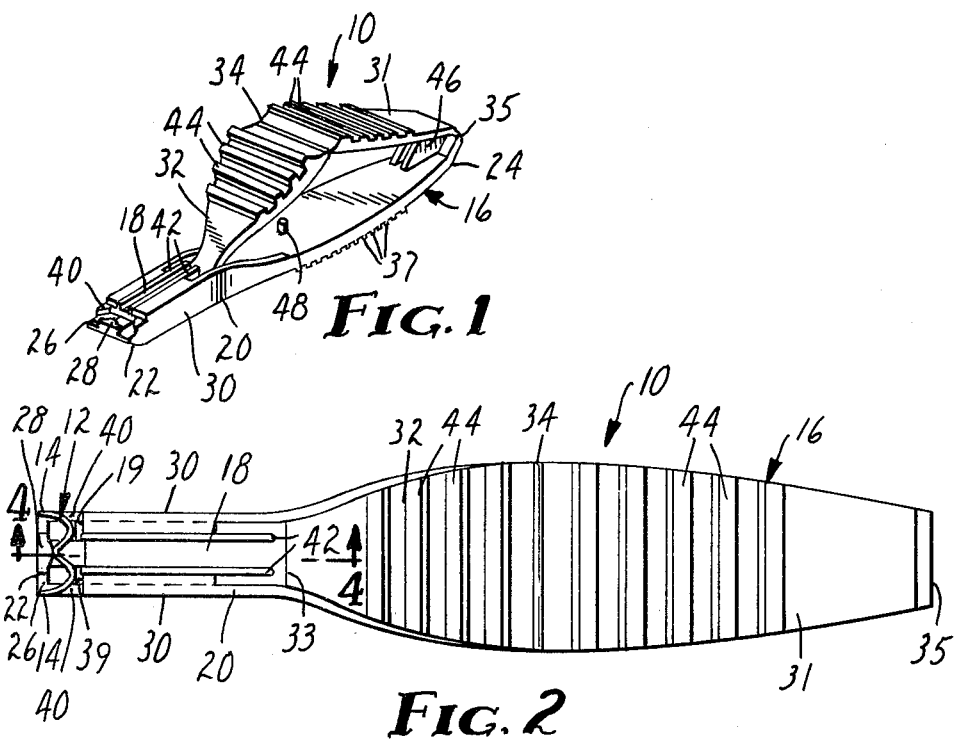
FIG. 1 is a perspective view of a first embodiment of a stapler according to the present invention.
Figure 2:
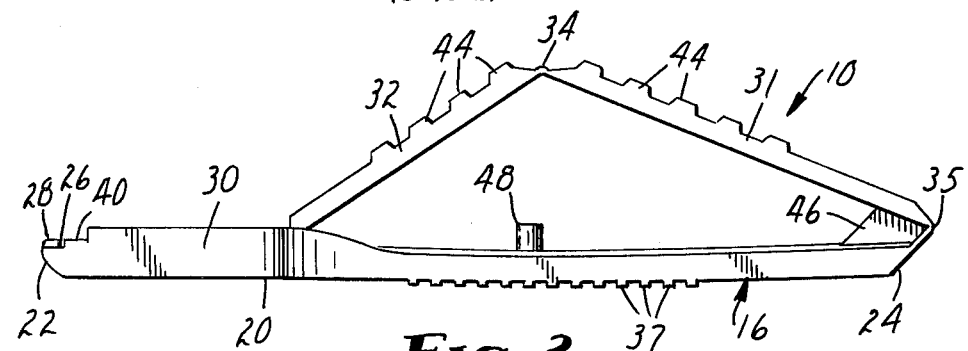
FIG. 2 is an enlarged top view of the stapler shown in FIG. 1.
Figure 3:
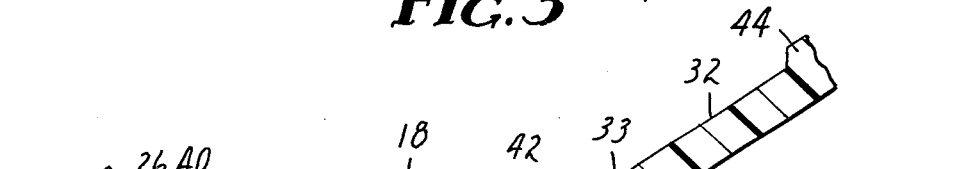
FIG. 3 is a side view of the stapler shown in FIG. 1.
Figure 4:
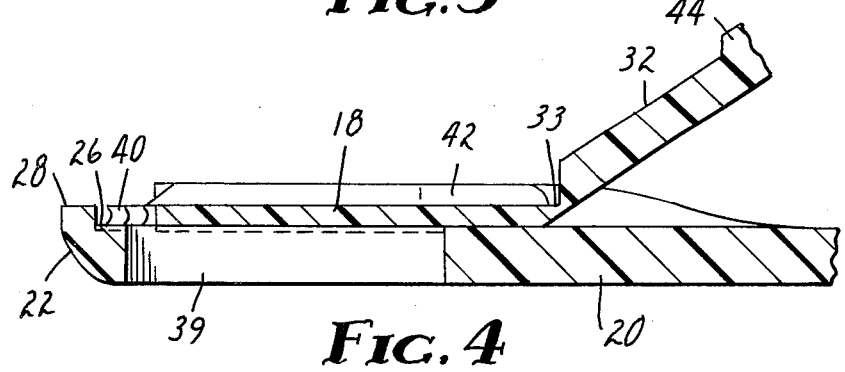
FIG. 4 is an enlarged fragmentary sectional view taken approximately along line 4—4 of FIG. 2.

Referring now to the drawing there is shown in FIGS. 1 through 8 a first embodiment of a stapler according to the present invention generally designated by the reference numeral 10.

The stapler 10 is adapted for joining disunited skin by closing a staple 12 which, when open (see FIGS. 2 and 5), is generally W-shaped, has a planar side surface, and has points 14 on its opposite ends. The stapler 10 comprises an elongate polymeric molding 16 (see FIG. 8) including a ram portion or ram 18 at one end having a distal end surface 19 adapted to engage the edge surface of the staple 12 opposite its points 14, and a body portion or body 20 at its end opposite the ram 18. The body 20 comprises a front end 22 at one end of the molding 16 and an opposite rear end 24, a staple guide surface 26 adjacent its front end 22, an anvil 28 transversely centered at its front end 22 projecting at a right angle to the staple guide surface 26, means adapted for mounting the staple 12 on the body 20 between its rear end 24 and the anvil 28 with one planar side surface of the staple 12 along the staple guide surface 26 and the points 14 of the staple 12 adjacent the front end 22 of the body 20, and means including opposed side walls 30 adapted for receiving the ram 18 on the body 20 for sliding movement from an open position with the end surface 19 of the ram 18 spaced from the anvil 28 to afford space for the open stable 12 therebetween (FIGS. 1 through 5) to a closed position (FIG. 7) to cause the end surface 19 of the ram 18 to engage and bend the staple 12 closed around the anvil 28. The molding 16 also includes first and second drive portions or members 31 and 32 between the body 20 and the ram 18, a first thin transverse section 33 pivotably joining the ram 18 to the second drive member 32, a second thin transverse section 34 pivotably joining the drive members 31 and 32, and a third thin transverse section 35 joining the ends of the body 20 and the first drive member 31. The molding 16 can be bent at the thin sections 33, 34 and 35 to engage the ram 18 with the side walls 30 by inserting the distal end of the ram 18 between the ends of the side walls 30 opposite the anvil 28 and sliding the ram 18 between the side walls 30 until its end surface 19 contacts the open staple 12. In the open position of the ram 18 (see FIGS. 1 through 5) the drive members 31 and 32 project away from the body 20 to provide a single toggle joint linkage adapted to be manually pressed toward the body 20 to move the ram 18 to its closed position to close the staple 12 around the anvil 28.

Means are provided on the side of the body 20 opposite the single toggle joint linkage for affording manual gripping of the body 20 during manual movement of the toggle joint linkage toward the body 20. This means comprises optional transverse outwardly-projecting ridges 37 on the outer surface of the body 20 opposite the drive members 31 and 32 which restrict slippage of the user's fingers. Also the body 20 has a slightly arcuate cross section which both provides a slightly concave outer surface at the ridges 37 to receive a user's finger, and with the side walls 30 adjacent the anvil 28 restricts bending of the body 20 when force is applied to close the staple 12. The side walls 30 include lips projecting toward each other and spaced from the adjacent portion of the body 20, which spaces between the lips and adjacent portions of the body 20 receive and position edge portions of the ram 18 in a predetermined track extending longitudinally along the body 20. The lips project over elongate openings 39 in the adjacent portion of the body 20, which openings 39 facilitate molding of the lips.

The means adapted for mounting the staple 12 on the body 20 include undercut projections 40 at the ends of the side walls 30 adjacent the anvil 28 and an undercut portion of the anvil 28 adjacent the side walls 30 which receive opposite sides of the staple 12 at spaced locations to position its planar side surface against the staple guide surface 26, its central portion against the anvil 28, and its points 14 about flush with the front end 22 of the body flanking and equally spaced from the anvil 28. The staple 12 can be releasably engaged with the projections 40 and anvil 28 to hold it in position prior to closing, and after a first staple 12 is closed, a second staple may be manually loaded into and closed by the stapler 10 if desired.

The ram 18 has longitudinally-extending reinforcing ribs 42 which project upwardly from the ram 18 and center it between the lips on the side walls 30. A notch is centrally located across the end surface 19 of the ram 18 to receive the anvil 28 when the ram 18 is in its closed position, and the portions of the end surface 19 flanking the notch are centrally grooved in a direction parallel to the guide surface 26 to receive the edge surface of the staple 12 and help keep it in alignment with the guide surface 26 as it is closed.

The drive members 31 and 32 have optional transverse ridges 44 on their surfaces that are opposite the body 20 when the ram 18 is in its open position to facilitate the grip of a user.

The stapler 10 also includes means for biasing the ram 18 toward its open position after it is moved toward its closed position so that the ram 18 will separate from the closed staple 12 and facilitate removal of the anvil 28 from within the closed staple 12 with a moderate release of manual pressure on the drive members 31 and 32. The molding 16 includes an abutment 46 provided by a pair of spaced triangular parts formed on the body 20 and located between parts of the body 20 and of the first drive member 31 when the molding 16 is bent at the thin transverse sections 33, 34 and 35 and the ram 18 is engaged between the side walls 30 and positioned in its open position. The third thin transverse section 35 and the abutment 46 then cantilever mount the first drive member 31 so that it must be bent to move the ram 18 to its closed position during manual application of force to the drive members 31 and 32. The first drive member 31 is sufficiently resilient so that it will recover to return the ram 18 to adjacent its open position after pressure is released therefrom. Also, a post 48 projects from the body 20 toward the juncture between the drive members 31 and 32 to preclude movement of the drive members into an over center locking position as they are pressed toward the body 20 to close the staple 12.

A preferred polymeric material for the molding 16 is the polycarbonate sold under the trade designation "Lexan" by General Electric Co., Schenectady, N.Y. which provides an acceptable combination of rigidity to afford forming of the staple by pressure from its surfaces, and flexibility for the thin transverse sections 33, 34 and 35 that allow them to be flexed without breaking for the small number of times required to close a small number of the staples 12. Other polymeric materials such as nylon, polypropylene, or high density polyethylene may also be suitable, however.

Figure 5:
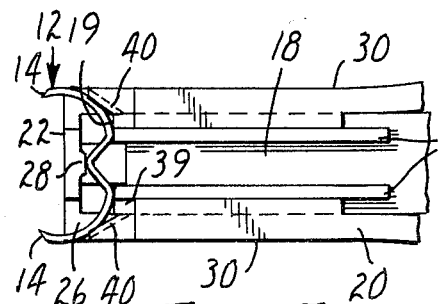
FIGS. 5, 6 and 7 are enlarged fragmentary top views of the stapler shown in FIG. 1 which sequentially illustrate the forming of a staple by the stapler.
Figure 6:
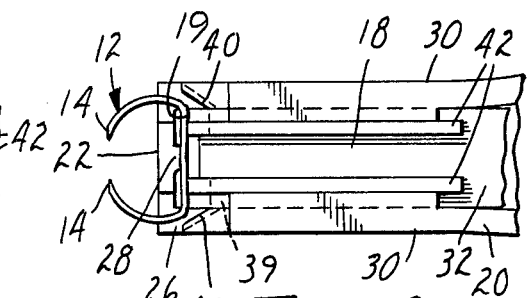
Figure 7:
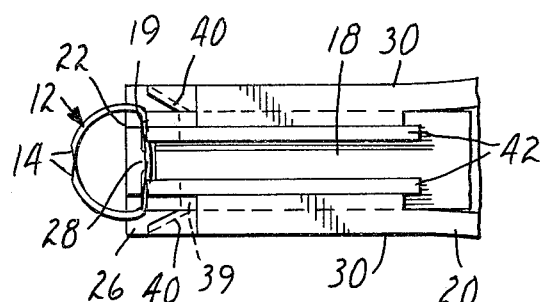
Figure 8:
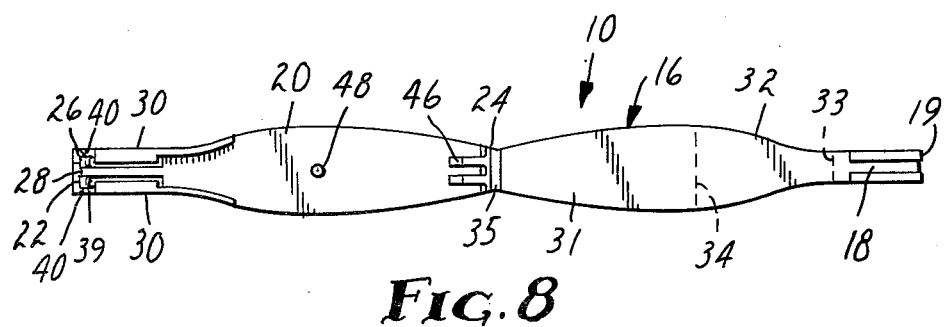
FIG. 8 is a top view of a molding comprising the stapler shown in FIG. 1.

The staple 12 is preferably of implant grade stainless steel, but could be made of other biologically acceptable metals such as some cobalt/chrome alloys. As shown in FIGS. 5, 6 and 7 the W-shaped open staple 12 is closed to a generally D-shaped closed staple 12 as is described in U.S. Pat. No. 4,185,762 (incorporated herein by reference). In addition to the advantages with respect to the patient in which it is inserted described in U.S. Pat. No. 4,185,762, the generally W-shaped staple 12 provides the advantage of being closeable with a short movement of the ram between its open and closed position which allows a relatively small toggle joint linkage and facilitates a compact design for the stapler 10; while being closeable by a simple planar end surface normal to the length of the ram 18 rather than requiring the spaced staple-forming projections used in the stapler of U.S. Pat. No. 4,202,480 which might have strength problems when made of polymeric materials.

Figure 9:
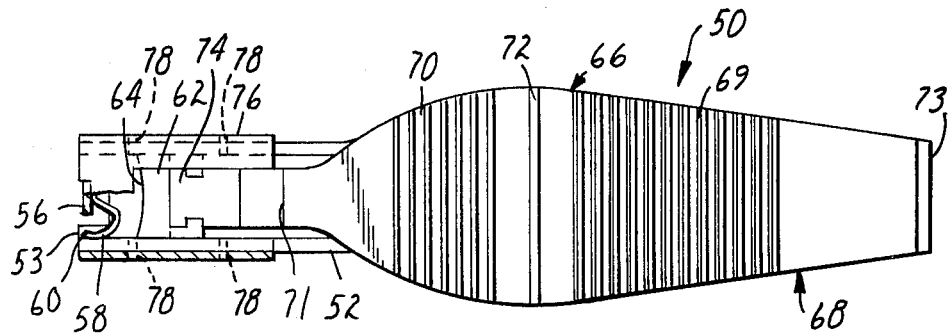
FIG. 9 is a top view of a second embodiment of a stapler according to the present invention having parts broken away to show detail.
Figure 10:
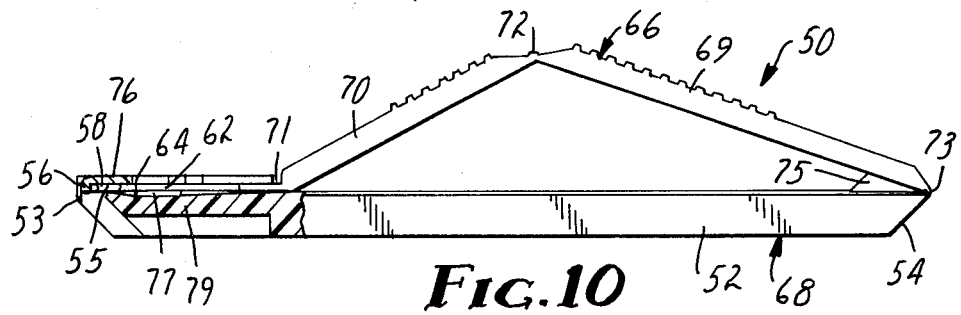
FIG. 10 is a side view of the stapler of FIG. 9 having parts broken away to show detail.

FIGS. 9 and 10 illustrate a second embodiment of a stapler according to the present invention generally designated by the reference numeral 50.

Like the stapler 10, the stapler 50 is adapted for joining living tissue and comprises an elongate body 52 having front and rear ends 53 and 54, a guide surface 55 adjacent its front end 53, and an anvil 56 transversely centered at its front end 53 projecting at a right angle to the guide surface 55. Means are provided for mounting an open, generally W-shaped staple 58 having a generally planar side surface and pointed ends or points 60 on the body 52 adjacent the anvil 56 with the side surface of the staple 58 along the guide surface 55 and the points 60 of the staple 58 adjacent its front end 53. A ram 62 having an end surface 64 adapted to engage the edge surface of the staple 58 opposite its points 60 is mounted by means on the body 52 for movement from an open position with the end surface 64 of the ram 62 spaced from the anvil 56 to afford space for the open staple 58 therebetween to a closed position to cause the end surface of the ram 62 to engage and bend the staple closed around the anvil 56. A single toggle joint linkage 66 is attached between the rear end 54 of the body and the ram 62, which toggle joint linkage 66 has axes of pivotal movement that are parallel to the guide surface 55 so that the toggle joint assembly 66 projects from the body 52 in the open position of the ram 62 and is manually movable toward the body 52 to move the ram 62 to its closed position.

Also like the stapler 10, the stapler 50 comprises a polymeric molding 68 including first and second drive portions or members 69 and 70 that provide the toggle joint linkage 66 between the body 52 and ram 62, a first thin transverse section 71 pivotably joining the ram 62 to the second drive member 70, a second thin transverse section 72 pivotably joining the drive members 69 and 70, and a third thin transverse section 73 joining the rear end 54 of the body 52 and the first drive member 69. Parts of the body 52 and the first drive member 69 are spaced apart by an abutment 75 formed on the body 52 that provides means for biasing the first drive member to its open position by requiring it to resiliently bend so that it can move the ram 62 to its closed position.

Unlike the stapler 10, however, the body 52 of the stapler 50 is formed both by a part of the molding 68 and by a metal cover 76 fixed to the molding 68 by pins 78 and spaced from a portion of the molding 68 to provide a guide channel for the ram 62 therebetween. The guide surface 55 for the staple 58 and the anvil 56 are formed on the cover 76. Also, the stapler 50 includes means for storing a reserve staple 77 within an opening in the body 52, which reserve staple 77 is pressed against the ram 62 by the distal end portion of a cantilevered spring-like portion 79 of the body 52. The reserve staple 77 can be moved onto the guide surface 55 by manually pulling the ram 62 to a third load position on the side of its open position opposite its closed position by lifting the drive members 69 and 70 away from the body 52, whereupon the spring-like portion 79 of the body 52 will move the reserve staple 77 so that it engages the guide surface 55 on the inner side of the cover 76, and subsequent movement of the ram 62 back to its open position will cause the ram 62 to move the reserve staple 77 to a position in engagement with the anvil 56, so that it can be closed by subsequent movement of the ram 62 to its closed position.

Also, the ram 62 of the stapler 50 is formed both by a part of the molding 68 and by a metal end plate on which the end surface 64 is formed. The molding and end plate parts of the ram 62 are locked together by a T-shaped tab 74 on the molding 68 that engages a mating slot through the end plate.

Figure 11:
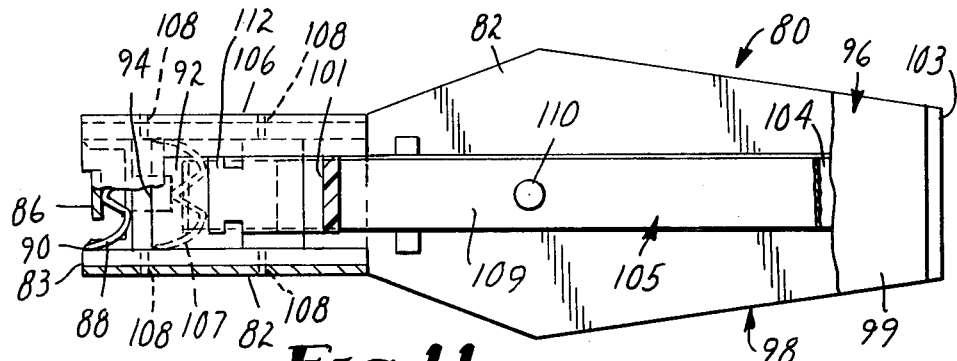
FIG. 11 is a top view of a third embodiment of a stapler according to the present invention having parts broken away to show detail.
Figure 12:
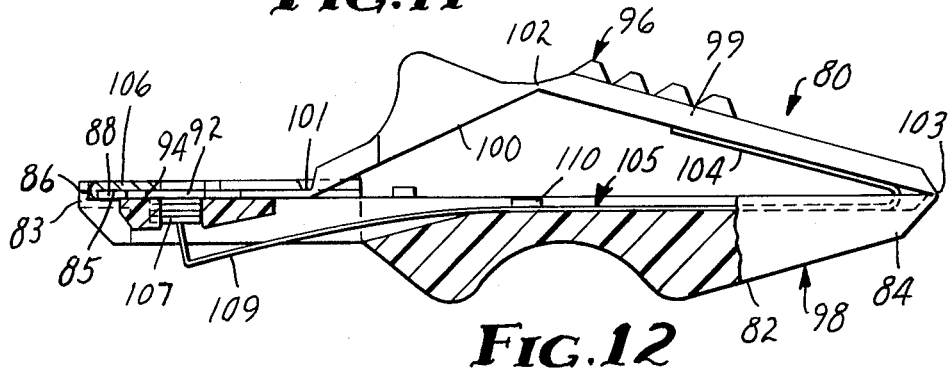
FIG. 12 is a side view of the stapler shown in FIG. 11 having parts broken away to show detail.

FIGS. 11 and 12 illustrate yet a third embodiment of a stapler according to the present invention generally designated by the reference numeral 80.

Like the staplers 10 and 50, the stapler 80 is adapted for joining living tissue and comprises an elongate body 82 having front and rear ends 83 and 84, a guide surface 85 adjacent its front end 83, and an anvil 86 transversely centered at its front end 83 projecting at a right angle to the guide surface 85. Means are provided for mounting an open, generally W-shaped staple 88 having a generally planar side surface and pointed ends or points 90 on the body 82 between its rear end 84 and the anvil 86 with the side surface of the staple 88 along the guide surface 85 and the points 90 of the staple 88 adjacent the front end 83 of the body 82. A ram 92 having an end surface 94 adapted to engage the edge surface of the staple 88 opposite its points 90 is mounted by means on the body 82 for movement from an open position with the end surface 94 of the ram 92 spaced from the anvil 86 to afford space for the open staple 88 therebetween to a closed position to cause the end surface 94 of the ram 92 to engage and bend the staple 88 closed around the anvil 86. A toggle joint linkage 96 is attached between the rear end 84 of the body 82 and the ram 92, which toggle joint linkage 96 has axes of pivotal movement that are parallel to the guide surface 85 so that the toggle joint linkage 96 projects from the body 82 in the open position of the ram 92 and is manually movable toward the body 82 to move the ram 92 to its closed position.

Also like the staplers 10 and 50, the stapler 80 comprises a polymeric molding 98 including first and second drive portions or members 99 and 100 that provide the toggle joint linkage 96 between the body 82 and ram 92, a first thin transverse section 101 pivotably joining the ram 92 to the second drive member 100, a second thin transverse section 102 pivotably joining the drive members 99 and 100, and a third thin transverse section 103 pivotably joining the rear end 84 of the body 82 and the first drive member 99. Unlike the other embodiments, however, a U-shaped end portion 104 of a spring 105 fixed to the body 82 by a rivet 110 provides means for biasing the first drive member 99 to its open position rather than by requiring the first drive member 99 to be resiliently bent upon movement of the ram 92 to its closed position. Also, the body 82 and drive portions 99 and 100 have much larger transverse ridges 111 that locate the fingers during use of the stapler 80, which ridges 111 on the side of the body 82 opposite the toggle joint linkage 96 provide means for affording manual gripping of the body 82 during manual movement of the toggle joint linkage 96 toward the body 82.

Like the body 52 of the stapler 50, the body 82 of the stapler 80 also is formed both by a part of the molding 98 and by a metal cover 106 fixed to the molding by pins 108 and spaced from the part of the molding 98 to provide a guide channel for the ram 92 therebetween. The guide surface 85 for the staple 88 and the anvil 86 are formed on the cover 106. Also, the stapler 80 includes means for storing a small number of reserve staples 107 (e.g., at least 4 or 5 and conceivably up to 15) within an opening in the body 82, which reserve staples 107 are pressed against the ram 92 by an L-shaped distal end portion 109 of the spring 105 opposite the portion 104.

The reserve staples 107 can be moved singly onto the guide surface 85 by manually pulling the ram 92 to a third load position on the side of its open position opposite its closed position by lifting the drive members 99 and 100 away from the body 82 (which lifting is facilitated by the U-shaped portion 104 of the spring 105), whereupon the L-shaped end portion 109 of the spring 105 will move the reserve staples 107 so that the reserve staple 107 adjacent the cover 106 engages the guide surface 85, and subsequent movement of the ram 92 back to its open position will cause the ram 92 to move the reserve staple 107 engaging the guide surface 85 to a position in engagement with the anvil 86, so that it can be closed by subsequently moving the ram 92 to its closed position.

Also, like the ram 62 of the stapler 50, the ram 92 of the stapler 80 is formed both by a part of the molding 98 and by a metal end plate on which the end surface 94 is formed. The molding 98 and the end plate of the ram 92 are locked together by a T-shaped tab 112 on the molding 98 that engages a mating slot through the end plate.

It will be understood that the stapler embodiments 10, 50, and 80 disclosed herein may be subject to many modifications and alterations without departing from the scope of the invention. For example, the metal end plates on the rams of the staplers 50 and 80 could be shaped like that of the ram in U.S. Pat. No. 4,202,480 and one or more generally U-shaped staples could be applied via the stapler; or the body, ram, and the members forming the toggle joint linkage could be formed of metal, and the hinge points of the toggle joint linkage could be joined by conventional hinge pin structures or by flexible connecting material such as tape. Thus the scope of the present invention should not be limited by the structures of the embodiments disclosed, but only by the structure described by language of the claims and its equivalents.

I claim:

1. A stapler adapted for joining living tissue, said stapler comprising an elongate body having front and rear ends, a guide surface adjacent said front end, and an anvil transversely centered at said front end projecting at a right angle to said guide surface; an open staple having a generally planar side surface and pointed ends; means for mounting said staple on said body adjacent said anvil with the side surface of said staple along said guide surface and the pointed ends of said staple adjacent the front end of said body; a ram having an end surface adapted to engage the edge surface of said staple opposite said pointed ends; means mounting said ram on said body for movement from an open position with the end surface of said ram spaced from said anvil to afford space for the open staple therebetween to a closed position to cause the end surface of said ram to engage and bend said staple closed around said anvil; only a single toggle joint linkage, said toggle joint linkage being attached between the rear end of said body and said ram with the axes of pivotal movement of said toggle joint linkage parallel to said guide surface so that said toggle joint linkage projects from said body in the open position of said ram and is manually movable toward said body to move said ram to its closed position; and means on the side of said body opposite said toggle joint linkage for affording manual gripping of said body during manual movement of said toggle joint linkage toward said body.

2. A stapler according to claim 1 further including means for biasing said ram to said open position.

3. A stapler according to claim 1 wherein said open staple is generally W-shaped when viewed from said planar side surface.

4. A stapler according to claim 1 wherein said toggle joint linkage comprises first and second drive members having adjacent pivotably-attached ends, the end of said first drive member opposite said adjacent ends is attached to said body adjacent said rear end, the end of said second drive member opposite said adjacent ends is pivotably attached to said ram, said drive members and ram are sufficiently long that said adjacent pivotably-attached ends of said drive members are spaced from said body in the open position of said ram, and said drive members are manually movable toward said body to move said ram to its closed position.

5. A stapler according to claim 4 wherein said body, said anvil, said means for mounting said staple, said ram, said means mounting said ram on said body, and said first and second drive members are a unitary polymeric molding.

6. A stapler according to claim 4 wherein said drive members and at least parts of said body and said ram are a unitary polymeric molding.

7. A stapler according to claim 6 wherein said polymeric molding includes a first thin, flexible, transverse section pivotably joining said ram to said second drive member, a second thin, flexible, transverse section pivotably joining said drive members, a third thin, flexible, transverse section joining the ends of said body and first drive member, and an abutment between parts of said body and said first drive member adjacent said third flexible transverse section which with said third thin transverse section cantilever mounts said first drive member to require resilient bending of said first drive member to move said ram from its open to its closed position.

8. A stapler according to claim 5 wherein said polymeric molding includes a first thin, flexible, transverse section pivotably joining said ram to said second drive member, a second thin, flexible, transverse section pivotably joining said drive members, a third thin, flexible, transverse section joining the ends of said body and first drive member, and an abutment between parts of said body and said first drive member adjacent said third flexible transverse section which with said third thin transverse section cantilever mounts said first drive member to require resilient bending of said first drive member to move said ram from its open to its closed position.

9. A stapler according to claim 4 further including at least one reserve staple and means for biasing said reserve staple toward a portion of said guide surface and against a side surface of said ram overlying said portion of said guide surface when said ram is in said open and closed positions, and wherein said ram is movable to a load position upon manual manipulation of said drive members, at which load position the end surface of said ram is spaced a greater distance from said anvil than at said open position to afford movement of said reserve staple against said portion of said guide surface and subsequent movement of said reserve staple to said anvil and closing of said reserve staple around said anvil upon movement of said ram through said open position to said closed position.

10. A stapler according to claim 9 wherein said stapler includes a plurality of said reserve staples.

11. A stapler adapted for joining disunited skin with a generally W-shaped staple having points on its opposite ends, said stapler comprising an elongate polymeric molding, said molding including a ram portion at one end having a distal end surface adapted to engage the edge surface of a said staple opposite its points; a body portion at the end of said molding opposite said ram portion, said body portion comprising a front end at the distal end of said molding and an opposite rear end, a guide surface adjacent said front end, an anvil transversely centered at said front end projecting at a right angle to said guide surface, means adapted for mounting said staple on said body portion adjacent said anvil with the side surface of said staple along said guide surface and the points of said staple adjacent the front end of said body portion, and means adapted for receiving said ram on said body portion for sliding movement from an open position with the end surface of said ram spaced from said anvil to afford space for the open staple therebetween to a closed position to cause the end surface of said ram portion to engage and bend said staple closed around said anvil; first and second drive portions between said body and ram portions, a first thin transverse section pivotably joining said ram to said second drive portion, a second thin transverse section pivotably joining said drive portions, a third thin, transverse section joining the ends of said body portion and first drive portion, said sections being flexible to afford bending said molding to engage said ram portion with said means adapted for receiving said ram portion on said body portion and said drive portions projecting away from said body portion when said ram is in its open position to provide a toggle joint linkage adapted to be manually pressed toward the body portion to move the ram portion to its closed position to close a said staple around said anvil.

12. A stapler according to claim 11 wherein said molding further includes an abutment adapted to be positioned between parts of said body portion and said first drive portion when said molding is bent to position said ram portion in its open position so that said third transverse section and said abutment cantilever mount said first drive portion to require manual resilient bending thereof to move said ram portion to its closed position.

* * * * *